(12) United States Patent
Gupta et al.

(10) Patent No.: US 9,539,005 B2
(45) Date of Patent: Jan. 10, 2017

(54) SURGICAL FASTENER DEPLOYMENT SYSTEM

(71) Applicant: C.R. Bard, Inc., Murray Hill, NJ (US)

(72) Inventors: Saurav V. Gupta, Medway, MA (US); Kevin J. Ranucci, Warwick, RI (US); Alan Bachman, Milford, CT (US); Scott Reed, Winchester, CT (US)

(73) Assignee: C.R. Bard, Inc., Murray Hill, NJ (US)

( * ) Notice: Subject to any disclaimer, the term of this patent is extended or adjusted under 35 U.S.C. 154(b) by 330 days.

(21) Appl. No.: 14/075,493

(22) Filed: Nov. 8, 2013

(65) Prior Publication Data

US 2015/0133966 A1 May 14, 2015

(51) Int. Cl.
*A61B 17/068* (2006.01)
*A61B 17/064* (2006.01)
*A61B 17/08* (2006.01)
A61B 17/00 (2006.01)

(52) U.S. Cl.
CPC ......... *A61B 17/068* (2013.01); *A61B 17/0644* (2013.01); *A61B 17/0684* (2013.01); *A61B 17/083* (2013.01); *A61B 2017/00867* (2013.01); *A61B 2017/0645* (2013.01); *A61B 2017/0649* (2013.01)

(58) Field of Classification Search
CPC ... A61B 17/10; A61B 17/068; A61B 17/0684; A61B 17/083; A61B 17/0644
See application file for complete search history.

(56) References Cited

U.S. PATENT DOCUMENTS

| | | | |
|---|---|---|---|
| 5,413,584 | A | 5/1995 | Schulze |
| 7,344,544 | B2 | 3/2008 | Bender et al. |
| 7,458,978 | B1 | 12/2008 | Bender et al. |
| 7,473,258 | B2 | 1/2009 | Clauson et al. |
| 7,533,250 | B2 | 5/2009 | Chauvel et al. |
| 7,533,790 | B1 | 5/2009 | Knodel et al. |
| 7,727,245 | B2 | 6/2010 | Bender et al. |
| 7,744,610 | B2 | 6/2010 | Hausen |
| 8,066,720 | B2 | 11/2011 | Knodel et al. |
| 8,393,517 | B2 | 3/2013 | Milo |
| 2009/0036903 | A1* | 2/2009 | Ino ............... A61B 17/0684 606/143 |

(Continued)

FOREIGN PATENT DOCUMENTS

EP 14192138 3/2015

*Primary Examiner* — Thomas McEvoy
(74) *Attorney, Agent, or Firm* — Wolf, Greenfield & Sacks, P.C.

(57) ABSTRACT

A deployment device and an associated surgical fastener as well as their methods of use are disclosed. In one embodiment, the deployment device includes a restraining mechanism constructed and arranged to temporarily limiting movement of a surgical fastener back span. The surgical fastener includes two legs extending in a distal direction from opposing ends of the back span. The legs are in a first closed position with a first shape. The deployment device also includes a spreader configured and arranged to engage the legs of the surgical fastener in the first closed position. When the spreader is moved in a distal direction relative to the back span, the spreader spreads the legs of the surgical fastener from the first closed position to a second open position as the back span is limited from distally moving by the restraining mechanism.

36 Claims, 8 Drawing Sheets

(56) References Cited

U.S. PATENT DOCUMENTS

| | | |
|---|---|---|
| 2009/0039138 A1 | 2/2009 | Bender et al. |
| 2010/0191258 A1 | 7/2010 | Harris et al. |
| 2010/0191262 A1 | 7/2010 | Harris et al. |
| 2010/0191282 A1 | 7/2010 | Harris et al. |
| 2012/0111919 A1 | 5/2012 | Holcomb et al. |

* cited by examiner

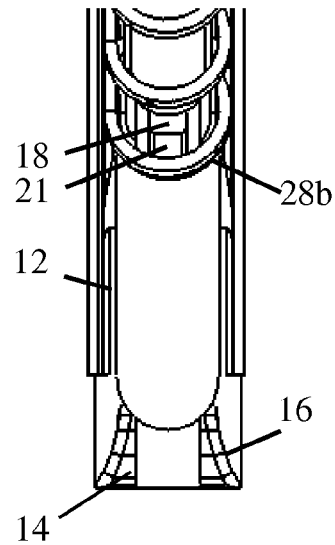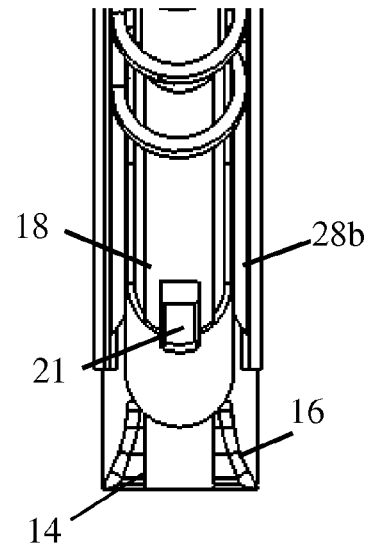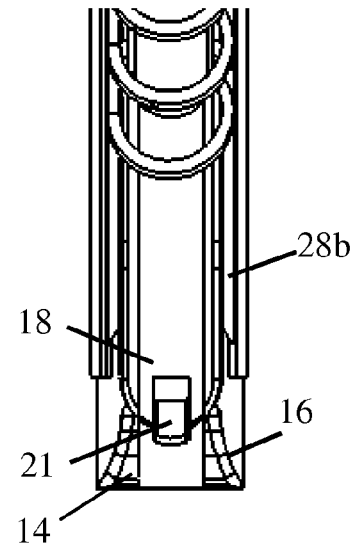
Fig. 4A  Fig. 4B  Fig. 4C
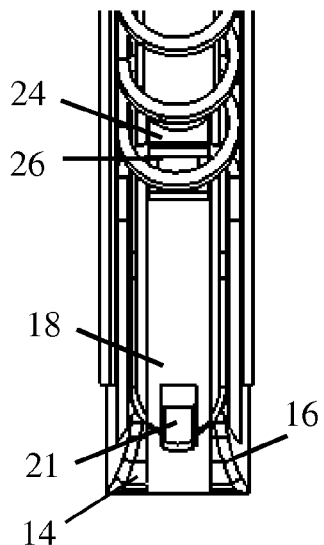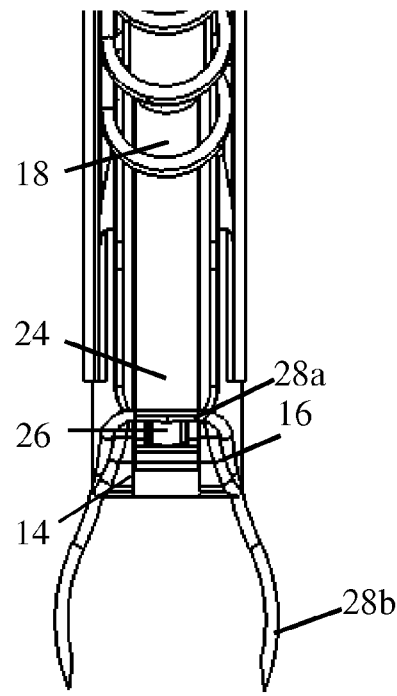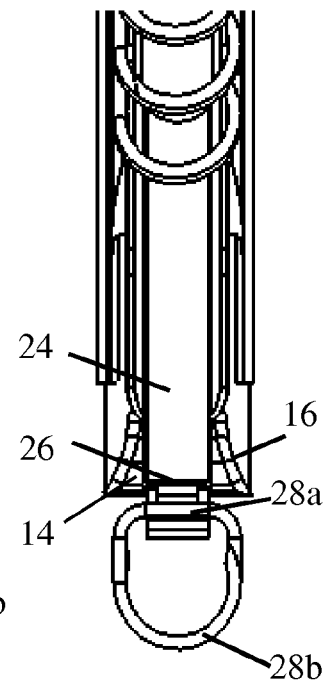
Fig. 4D  Fig. 4E  Fig. 4F

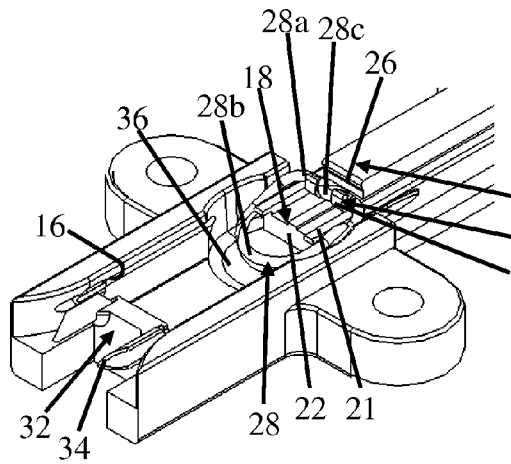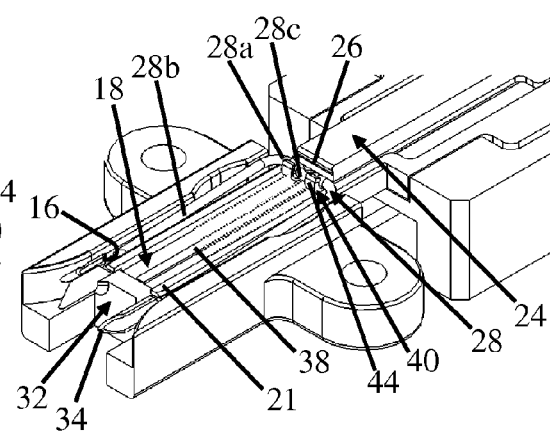
Fig. 10A    Fig. 10B
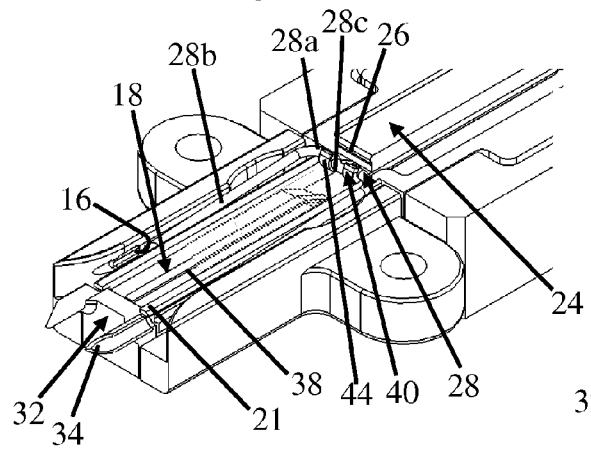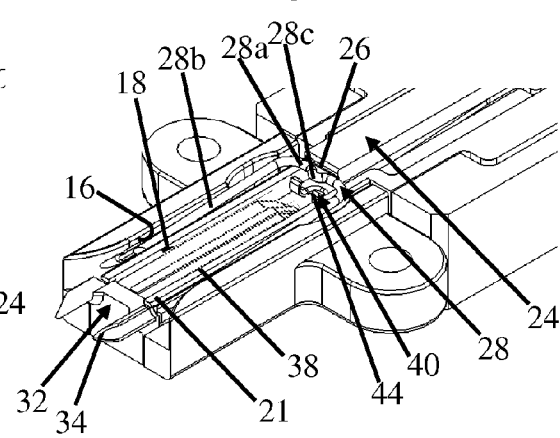
Fig. 10C    Fig. 10D
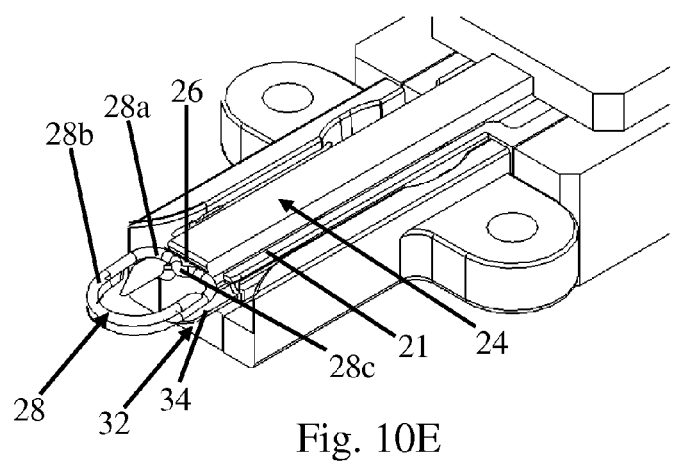
Fig. 10E

SURGICAL FASTENER DEPLOYMENT SYSTEM

FIELD

Disclosed embodiments are related to surgical fastener deployment systems.

BACKGROUND

Surgical fasteners are widely used in many different medical procedures. For example, staples, sutures, clips and other fasteners are commonly used in laparoscopic and open surgical procedures.

SUMMARY

In one embodiment, a deployment device includes a handle and an elongated shaft extending from the handle. At a distal end of the shaft, a restraining mechanism is constructed and arranged to temporarily limit distal movement of a back span of a surgical fastener. The surgical fastener includes two legs extending in a distal direction from opposing ends of the back span and the legs have a first closed position with a first shape. A spreader is configured and arranged to engage the legs of the surgical fastener in the first closed position. Moving the spreader in a distal direction relative to the back span spreads the legs of the surgical fastener from the first closed position to a second open position as the back span is limited from moving distally by the restraining mechanism.

In another embodiment, a method for deploying a surgical fastener includes: providing a deployment device including a surgical fastener at a distal end of the deployment device; limiting distal movement of a back span of the surgical fastener, wherein the surgical fastener includes two legs extending in a distal direction from opposing ends of the back span, wherein the legs are in a first closed position with a first shape; and pushing against an interior surface of the legs while movement of the back span is limited to spread the two legs to an open position.

In yet another embodiment, a surgical fastener includes a back span and two legs extending in a distal direction from opposing ends of the back span. The legs are in a first closed position with a first shape and are adapted to be opened to at least a straight orientation and automatically return to the first shape.

In another embodiment, a surgical fastener includes a back span and two legs extending in a distal direction from opposing ends of the back span. The legs are in a first closed position with a first shape and the back span is located in a plane that is above a plane in which the legs are located.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 4A is a schematic top view of a surgical fastener and the deployment mechanism prior to deployment;

FIG. 4B is a schematic top view of the surgical fastener and deployment mechanism of FIG. 4A during a subsequent deployment step;

FIG. 4C is a schematic top view of the surgical fastener and deployment mechanism of FIG. 4A during a subsequent deployment step;

FIG. 4D is a schematic top view of the surgical fastener and deployment mechanism of FIG. 4A during a subsequent deployment step;

FIG. 4E is a schematic top view of the surgical fastener and deployment mechanism of FIG. 4A during a subsequent deployment step;

FIG. 4F is a schematic top view of the surgical fastener and deployment mechanism of FIG. 4A during a subsequent deployment step;

FIG. 10A is a schematic perspective view of a surgical fastener and deployment mechanism prior to deployment;

FIG. 10B is a schematic perspective view of the surgical fastener and deployment mechanism of FIG. 10A during a subsequent deployment step;

FIG. 10C is a schematic perspective view of the surgical fastener and deployment mechanism of FIG. 10A during a subsequent deployment step;

FIG. 10D is a schematic perspective view of the surgical fastener and deployment mechanism of FIG. 10A during a subsequent deployment step; and FIG. 10E is a schematic perspective view of the surgical fastener and deployment mechanism of FIG. 10A during a subsequent deployment step.

DETAILED DESCRIPTION

Figure 1:
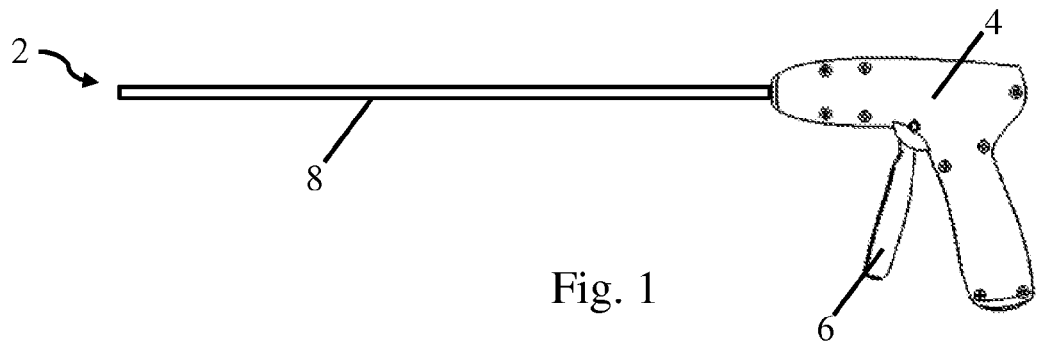
FIG. 1 is a schematic view of a surgical fastener deployment device.

The inventors have recognized the benefits associated with a surgical fastener capable of being spread to an open state and returned to a closed state using either superelasticity and/or shape memory effects. Since the surgical fasteners are capable of closing without the need to be separately formed, an associated deployment device does not need to include a separate mechanism for closing the surgical fasteners. This combination of a simplified deployment device and self-closing surgical fasteners may offer quick deployment of surgical fasteners, reduced actuation forces, a smaller profile deployment mechanism, reduced cost, and improved ease of manufacturing.

In one embodiment, a surgical fastener includes a back span and a pair of legs extending from opposing ends of the back span. The pair of legs may be shaped to overlap with one another along a portion of their lengths and form a closed loop. The legs may either touch, or be spaced from one another. Depending on the particular embodiment, the legs may curve to form a closed loop with a circular shape, though other shapes are also possible. One or more of the surgical fasteners may be sequentially arranged on a retainer, or other appropriate carrier, and may be sequentially provided to a deployment mechanism using any appropriate feeding mechanism or fastener magazine arrangement. Once a distal most fastener is removed from the retainer, the closed loop formed by the pair of legs may be engaged by a corresponding spreader and the back span may be held in place by an associated restraining mechanism. While engaged with the pair of legs, the spreader may be moved in a distal direction relative to the back span which is restrained by the restraining mechanism. Since the legs are engaged with the spreader and the back span is held by the restraining mechanism, the relative movement of the spreader and the back span of the surgical fastener applies a distally directed force to the legs which spreads the legs apart to an open position. As the legs are spread to the open position, one or more guiding features on the spreader and/or other components may be used to guide the legs to their desired positions for subsequent deployment. In other embodiments, the restraining mechanism may permit some distal movement of the back span while it is restrained. However, the spreader would still move distally relative to the back span in such an embodiment. Further, it is this movement of the spreader relative to the back span that results in the distally directed force being applied to the legs to spread them to the open position.

In addition to the spreader and the restraining mechanism, a pusher is positioned to engage the back span of the distal most fastener. With the fastener in the opened position, the restraining mechanism releases and/or permits the distal movement of the surgical fastener. The pusher then distally displaces the fastener to deploy the spread legs into tissue. Depending on the particular embodiment, the legs of the surgical fastener may be formed against an anvil or other appropriate feature as the pusher displaces the surgical fastener in a distal direction further spreading the legs of the surgical fastener. Once the pusher has fully deployed the surgical fastener, the back span of the surgical fastener is released from the pusher.

The surgical fastener may be made from a material exhibiting superelasticity and/or shape memory properties. Therefore, as the pair of legs are inserted into tissue, the pair of legs either spring back from the open position to the original closed loop shape due to superelasticity or the surgical fastener is warmed and the pair of legs return to the original closed loop shape due to the noted shape memory effect. It should be understood that a combination of the two effects may also occur. Several nonlimiting examples of appropriate materials exhibiting sufficient superelasticity and/or shape memory properties include super alloys such as nickel titanium alloys, iron nickel alloys, copper aluminum nickel alloys, and other appropriate bioresorbable or nonabsorbable metals. Additionally, in some embodiments, the surgical fasteners may be made from a polymer exhibiting shape memory properties. In such an embodiment, the polymer may also be bioresorbable. While specific materials are noted above, any material exhibiting sufficient superelasticity and/or shape memory properties could be used.

It should be understood that while in some embodiments the surgical fasteners have a closed loop shape and overlapping legs as described above, the current disclosure is not so limited. Instead, in some embodiments the legs of the surgical fastener might not overlap and the surgical fastener might have another shape. For example, the legs might form a C shape, a U shape, or any other appropriate shape. Alternatively, the surgical fastener might still form a closed loop, but the distal ends of the legs might be arranged end-to end such that they do not overlap one another. In view of the above, it should be understood that the surgical fasteners may have any desired shape and configuration.

In some embodiments the surgical fasteners return to their initial closed loop shape after being spread to the open position and deployed into tissue. However, in some embodiments, the surgical fastener may only partly return to the closed loop shape due to forces being applied to the legs of the surgical fastener from engaged tissue. Alternatively, some amount of unrecoverable permanent deformation of the surgical fastener might occur. Therefore, it should be understood that the current disclosure is meant to include embodiments in which the surgical fastener returns to its initial closed loop shape as well as embodiments in which the surgical fastener only partly returns to its initial closed loop shape. Further, in some embodiments the surgical fasteners might return to a shape that is smaller than the initial closed loop shape. For example, the surgical fasteners might include an initial amount of deformation when they are positioned in the deployment position. The surgical fasteners can then be further spread to the open position and recover to a shape smaller than the initial shape when they are deployed into tissue using a superelastic and/or shape memory effect. In other embodiments, the fastener may transform from an open shape to a final shape that is not closed.

The surgical fasteners may have any desired dimensions appropriate for their intended application. However, in one embodiment the surgical fasteners have a width that is between about 2 mm to 3 mm, 3 mm to 4 mm, 4 mm to 5 mm, or any other appropriate width. The surgical fastener may also include sufficient superelasticity and/or shape memory properties to fully recover from being spread to an open width between about the original width of the surgical fastener and 1 mm, 2 mm, 3 mm, 4, mm, or 5 mm wider than the original width of the surgical fastener or any other appropriate length. Both larger and smaller dimensions for the initial width of the fastener as well as the width of the open position are possible.

In addition to the surgical fasteners, the various components of the deployment device may also be made from any appropriate material or combination of materials including various appropriate metals and polymers. Appropriate materials include, but are not limited to: stainless steels such as 316L stainless steel; nickel titanium based alloys such as nitinol; polypropylene; high density polyurethane; ultrahigh molecular weight polyethylene (UHMWPE); nylon; polyester; or any other appropriate material.

For the sake of clarity, the currently disclosed embodiments are directed to a laparoscopic device. However, the current disclosure is not limited to laparoscopic devices. Instead, the currently disclosed surgical fasteners and associated deployment devices could be used in any appropriate device for the deployment of a surgical fastener into tissue. For example, any of the currently disclosed components, or combination of disclosed components, could be incorporated into an endoscopic device, a borescopic device, a catheter, a deployment device for use in "open" procedures, or any other appropriate deployment device. Additionally, the deployment device may be loaded with one or more fasteners prior to being provided to an end user, or it may be constructed to allow the user to load the instrument with one or more fasteners.

For the sake of clarity, the figures do not depict a feeding mechanism associated with the plurality of surgical fasteners. However, it should be understood that any appropriate feeding mechanism could be used to sequentially provide a plurality of surgical fasteners to the deployment mechanism. For example, a walking beam structure in which a reciprocating mechanism sequentially displaces either a stack of surgical fasteners or individually displaces each surgical fastener in a stack of surgical fasteners towards a deployment position could be used. Alternatively, a spring applying a distally directed force could be used to bias a stack of surgical fasteners towards a deployment position. Additionally, any appropriate mechanism capable of positioning the distal most surgical fastener in the deployment position might be used. Appropriate mechanisms can include springs, tabs, gravity assisted positioning, or any other mechanism or method capable of positioning the distal most surgical fastener in the deployment position. In view of the above, it should be understood that the feeding mechanism associated with the disclosed surgical fasteners and deployment device can be embodied in any number of different ways and the current disclosure is not limited in this fashion.

It should also be understood, that the various components described below in reference to the figures such as the spreader, pusher, former, anvil, and various guide structures can also be embodied in any number of different ways. Therefore, the current disclosure should not be limited to only the embodiments depicted in the figures and described herein.

Turning now to the figures, specific embodiments are described in more detail. However, it should be understood, that embodiments different from those depicted in the figures are also possible.

FIG. 1 depicts a deployment device 2 in the form of a laparoscopic instrument for deploying one or more surgical fasteners into a prosthetic and/or tissue. The deployment device 2 includes a handle 4 at a proximal end of the device and a trigger 6. The deployment device also includes an elongated shaft 8 extending in a distal direction from the handle 4. When the trigger 6 is actuated, a surgical fastener is deployed from a distal tip of the elongated shaft 8. It should be understood, that the deployed surgical fastener may be deployed into any appropriate prosthetic, tissue, or other target. A prosthetic may be embodied by any number of different components or materials. For example, in one embodiment, the prosthetic may be a soft tissue repair fabric, such as a surgical mesh, and used for repairing a hernia.

Figure 2:
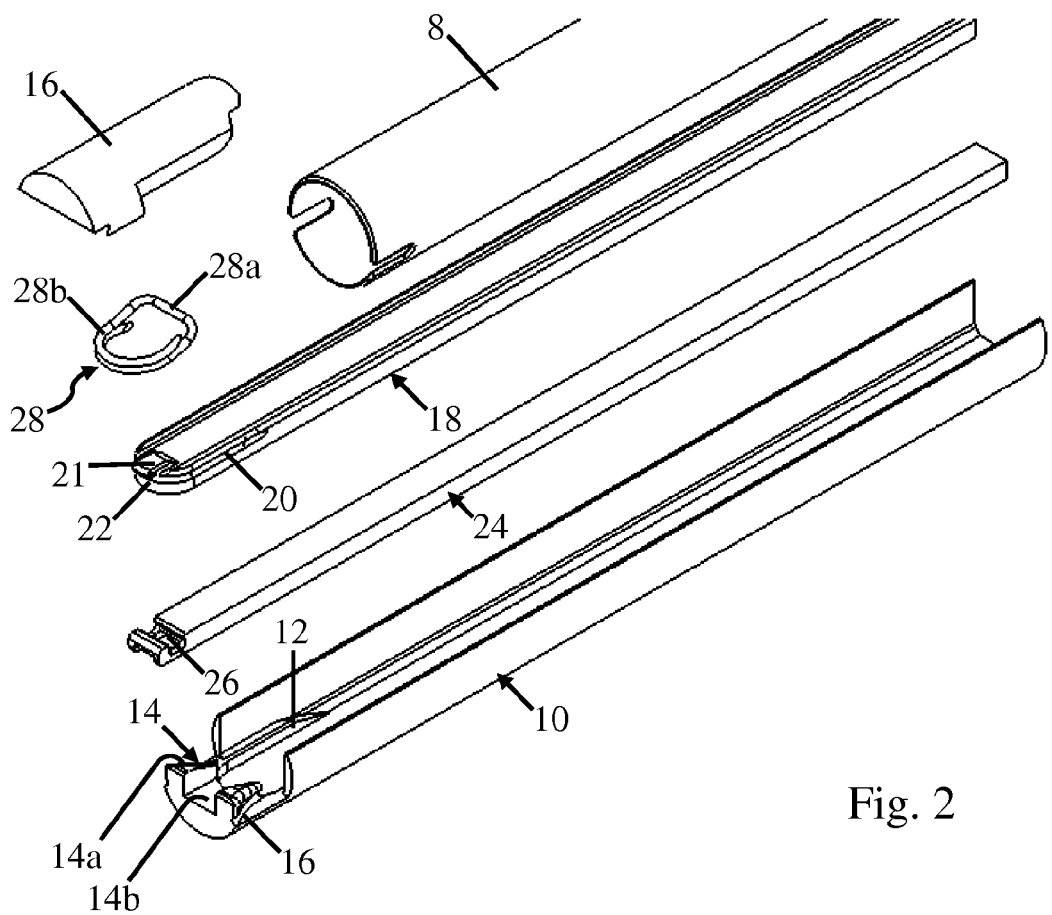
FIG. 2 is an exploded schematic view of the distal end of the surgical fastener deployment device.
Figure 3A:
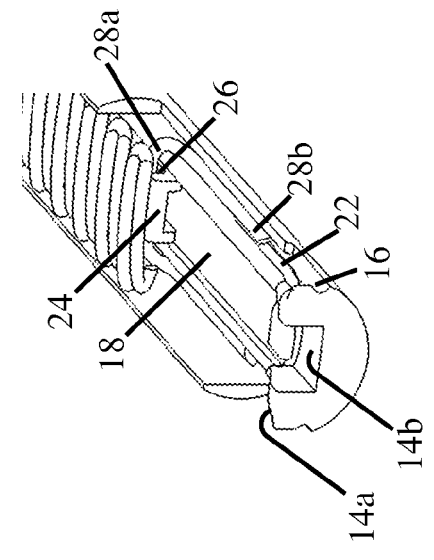
FIG. 3A is a schematic perspective view of a surgical fastener and the deployment mechanism prior to deployment.
Figure 3B:
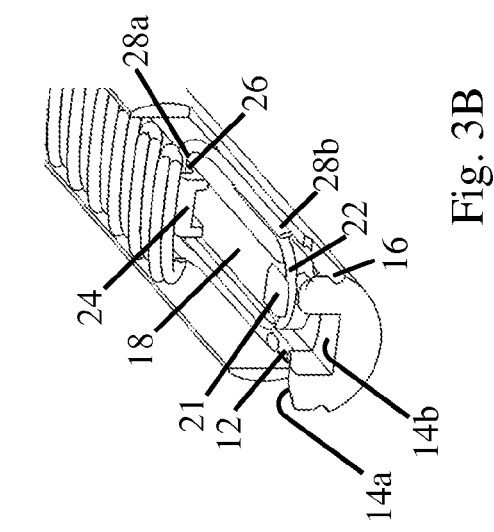
FIG. 3B is a schematic perspective view of the surgical fastener and deployment mechanism of FIG. 3A during a subsequent deployment step.
Figure 3C:
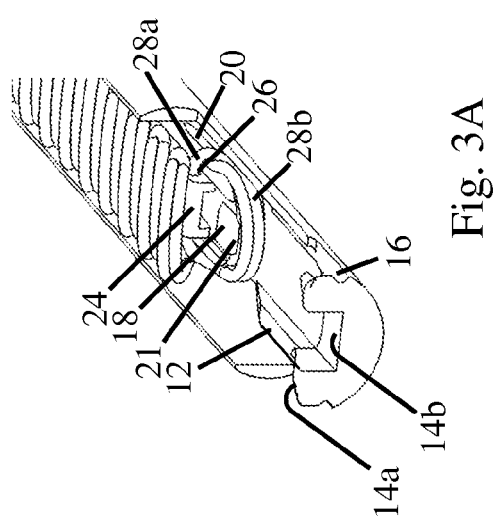
FIG. 3C is a schematic perspective view of the surgical fastener and deployment mechanism of FIG. 3A during a subsequent deployment step.
Figure 3D:
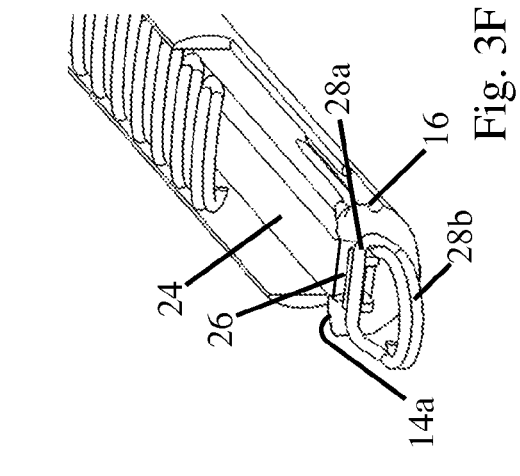
FIG. 3D is a schematic perspective view of the surgical fastener and deployment mechanism of FIG. 3A during a subsequent deployment step.
Figure 3E:
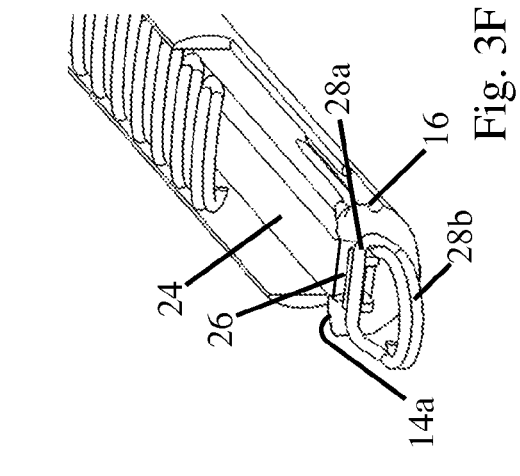
FIG. 3E is a schematic perspective view of the surgical fastener and deployment mechanism of FIG. 3A during a subsequent deployment step.
Figure 3F:
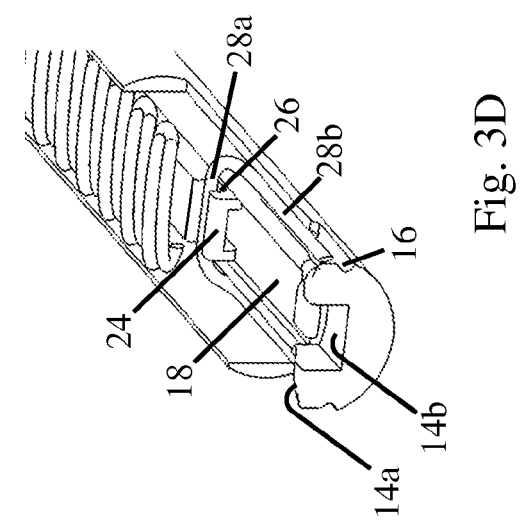
FIG. 3F is a schematic perspective view of the surgical fastener and deployment mechanism of FIG. 3A during a subsequent deployment step.
Figure 5A:
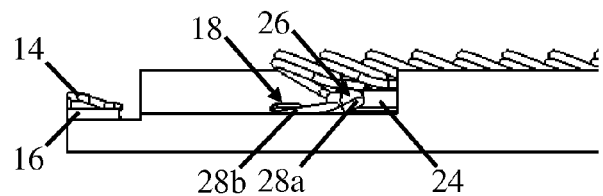
FIG. 5A is a schematic side view of a surgical fastener and a deployment mechanism prior to deployment.
Figure 5B:
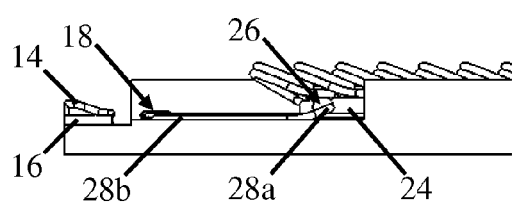
FIG. 5B is a schematic side view of the surgical fastener and deployment mechanism of FIG. 5A during a subsequent deployment step.
Figure 5C:
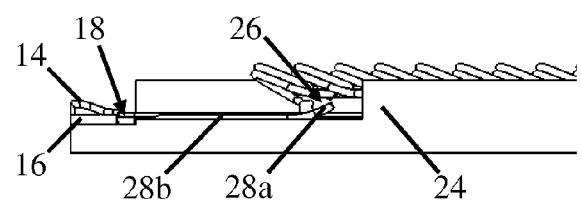
FIG. 5C is a schematic side view of the surgical fastener and deployment mechanism of FIG. 5A during a subsequent deployment step.
Figure 5D:
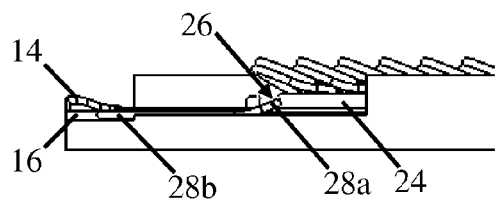
FIG. 5D is a schematic side view of the surgical fastener and deployment mechanism of FIG. 5A during a subsequent deployment step.
Figure 5E:
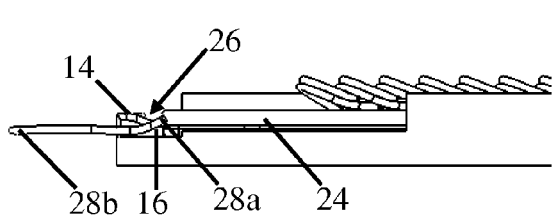
FIG. 5E is a schematic side view of the surgical fastener and deployment mechanism of FIG. 5A during a subsequent deployment step.
Figure 5F:
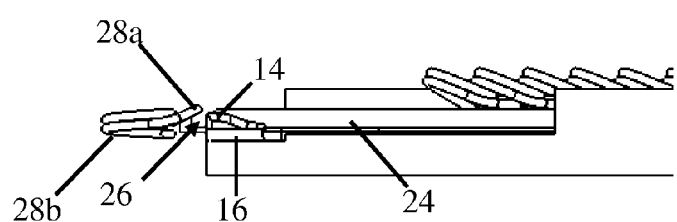
FIG. 5F is a schematic side view of the surgical fastener and deployment mechanism of FIG. 5A during a subsequent deployment step.

One specific embodiment of a deployment device is depicted in FIG. 2 which shows an exploded view of the various components disposed at the distal end of an elongated shaft 8. These components include a former 10, a spreader 18, and a pusher 24 as well as a cover 16 for covering those portions of these components that extend past a distal end of the elongated shaft 8. As described in more detail below, these components are used to deploy one or more surgical fasteners 28 from the distal end of the elongated shaft 8.

In the depicted embodiment, the surgical fastener 28 in a closed position includes a straight back span 28a and a pair of legs 28b extending in a distal direction from opposing ends of the back span. The pair of legs 28b are curved inwards and overlap each other for at least a portion of their lengths. The legs 28b include pointed tips that are adapted to pierce through an intended tissue and/or prosthetic. Additionally, in the depicted embodiment, the back span 28a is located in a plane that is above the plane in which the legs 28b are located in. Therefore, the legs 28b include a bend where they are joined to the back span 28a. While the legs 28b are depicted as touching one another, they may also be spaced apart from one another in some embodiments. Further, while the back span 28a has been depicted as being straight, other shapes including a curved back span, a back span including one or more bends, or other appropriate features might be used.

The former 10 includes one or more guide surfaces 12, a ramp 14, and an anvil 16 that collectively guide and form the surgical fastener during deployment. As depicted in the figure, the one or more guide surfaces 12 include a proximally located portion that slopes upwards towards a distally extending flat surface that extends up to the anvil 16. As described in more detail below, the sloped portion and the distally extending flat surface of the guide surfaces 12 help to guide the legs 28b of the surgical fastener 28 towards the anvil 16 as the legs of the surgical fastener are spread to the open position. Similar to the guide surfaces 12, the anvil 16 also guides the legs 28b of the surgical fastener during deployment. Specifically, the anvil 16 defines two outwardly oriented grooves that the legs 28b are pressed against in order to spread the legs to a width that is greater than a width of the original closed loop shape of the surgical fastener. In some embodiments the width that the anvil 16 spreads the legs 28b to is greater than a width of the elongated shaft 8. Unlike the one or more guide surfaces 12 and the anvil 16 which interact with the legs 28b of the surgical fastener, the ramp 14 is constructed and arranged to interact with the back span 28a of the surgical fastener in order to release the surgical fastener 28 at the end of deployment. As depicted in the figure, the ramp 14 includes raised portions 14a positioned above the anvil 16 and on opposing sides of a cutout 14b for accommodating distal movement of the pusher 24. The raised portions 14a are constructed and arranged to permit the back span 28a of the surgical fastener to cam over the raised portions of the ramp as it is deployed from the distal end of the elongated shaft. While specific constructions of the guide surfaces 12, the ramp 14, and the anvil 16 are depicted in the figure and described above, other alternative constructions are also possible.

The spreader 18 applies a force to an interior surface of the legs 28b of the surgical fasteners, spreading the legs to an open position. The spreader 18 includes a distal end 22, a groove 20, and an overhang 21, as shown in FIG. 2. More specifically, the distal end 22 is sized and shaped to engage with the interior surface of the legs 28b of the surgical fastener. While a rounded shape that complements a shape of the legs has been depicted, other shapes not complementing a shape of the legs, including a flat surface, might be used. The spreader 18 also includes a groove 20 that extends around the distal end 22 and along a portion of the sides of the spreader 18. The groove 20 is sized and shaped to accommodate the legs 28b of the surgical fastener. Therefore, as the spreader 18 spreads the legs 28b to the open position, the legs will become positioned in the groove 20 which may help to guide and position the legs for subsequent deployment. An overhang 21 extends distally outwards and is located above the distal end 22 of the spreader, though other arrangements are also possible. Therefore, when the surgical fastener 28 is positioned with the pair of legs 28b located below the overhang 21, the overhang 21 retains the legs 28b on the spreader 18 during spreading by preventing upwards movement of the legs 28b off of the distal end 22.

A slot 26 located at a distal end of the pusher is sized and shaped to receive the back span 28a of the surgical fastener. With the back span 28a of the surgical fastener retained in the slot 26 of the pusher, and the pusher 24 held stationary, distal movement of the back span 28a within the elongated shaft 8 is prevented when the spreader 18 advances against the legs 28b. In addition, when the pusher 24 is moved in a distal direction, the slot 26 will apply a distally directed force to the back span 28a to distally displace and deploy the surgical fastener 28. While a slot has been depicted, other appropriate features and/or separate components are contemplated to restrain and/or push the surgical fastener. For example, the slot might be replaced by hooks, posts, or other appropriate features.

FIGS. 3A-5F illustrate the deployment device and the surgical fastener during different stages of deployment. A wall of the former is removed in FIGS. 3A-3F for visualization purposes. The shape of the surgical fastener during these different stages of deployment are illustrated in FIGS. 6A-6E.

As depicted in these figures, the spreader 18 is disposed on the former and the pusher 24 is disposed on top of the spreader 18. Prior to actuation, a distal most surgical fastener 28 is positioned in an initial deployment position with its back span 28a disposed in the slot 26 of the pusher 24 which is located in a plane above the upper surface of the spreader, see FIGS. 3A, 4A, 5A, and 6A. The pair of legs 28b are also engaged with the distal end 22 of the spreader. In this initial position, the distal most surgical fastener 28 is still in its initial closed loop shape.

Figure 6A:
FIG. 6A is a schematic perspective view of a surgical fastener prior to deployment.
Figure 6B:
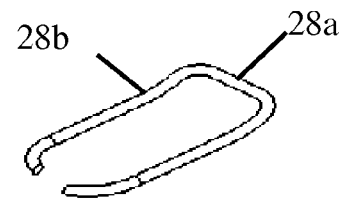
FIG. 6B is a schematic perspective view of the surgical fastener of FIG. 6A during a subsequent deployment step.
Figure 6C:
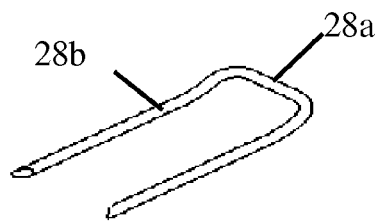
FIG. 6C is a schematic perspective view of the surgical fastener of FIG. 6A during a subsequent deployment step.
Figure 6D:
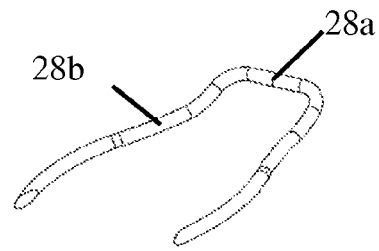
FIG. 6D is a schematic perspective view of the surgical fastener of FIG. 6A during a subsequent deployment step.
Figure 6E:
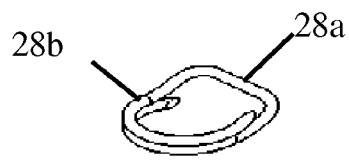
FIG. 6E is a schematic perspective view of the surgical fastener of FIG. 6A during a subsequent deployment step.

During the initial stages of actuation, the spreader 18 is moved in a distal direction while the pusher 24 is held stationary, see FIGS. 3B, 3C, 4B, 4C, 5B, and 5C. As the spreader 18 moves in the distal direction relative to the pusher, the distal end 22 of the spreader applies a distally directed force to the interior surfaces of the legs 28b of the surgical fastener. Since the back span 28a of the surgical fastener is held stationary by the pusher 24, the distally directed force spreads the legs 28b towards an open position. The groove 22 may be located in the same plane as the anvil 16. Therefore, as the legs 28 are spread, groove 22 helps to guide the legs 28b towards the anvil 16. Similarly, as the legs are spread, the guide surfaces 12 on the former 10 also help to guide the legs 28b up the sloped proximal portion of the guide surfaces 12 and onto the distally extending flat surfaces towards the anvil 16. As the distal movement of the spreader 18 continues, the legs 28b of the surgical fastener are spread from the closed loop initial shape to an open position where the legs are straight, though other open configurations of the legs are also possible. The partially opened position and the fully opened position of the legs 28b are depicted in FIGS. 6B and 6C. After opening the legs 28b to the fully opened position, distal movement of the spreader 18 continues until it contacts a proximal surface of the ramp 14. However, distal movement of the spreader 18 could be stopped at any point after the legs of the surgical fastener have been opened in other embodiments.

Once the legs 28b of the surgical fastener have been spread to the open position, the pusher 24 is moved in a distal direction. Since the back span 28a of the surgical fastener is positioned in the slot 26 of the pusher, the pusher 24 applies a distally directed force to the back span 28a and the surgical fastener is displaced in the distal direction. As the surgical fastener is moved in the distal direction, the back span 28a is displaced in a plane above the spreader 18. The legs 28b are displaced along the guide surfaces 12 of the former and are retained at least partially in the groove 22 of the spreader in order to guide the legs towards the anvil 16 and maintain them in the open position, see FIGS. 3D, 4D, 5D, and 6D.

As distal movement of the pusher 24 continues, the distal ends of the legs 28b contact the anvil 16. The anvil 16 is constructed and arranged such that the legs 28b are pressed against the anvil and displaced outwards as the surgical fastener is moved in the distal direction. In certain embodiments, the anvil is constructed and arranged such that the legs are displaced to a width that is greater than a width of the initial closed loop shape of the surgical fastener. Further, in some instances this width may be greater than a width of the elongated shaft that the surgical fasteners are disposed within.

As distal movement of the pusher 24 continues, the pusher 24 enters the cut out 14b located in the ramp and the back span 28a of the surgical fastener cams over the raised portions 14a of the ramp. As the back span 28a of the surgical fastener is displaced upwards out of the slot 26, the surgical fastener is released from the deployment device, see FIGS. 3F, 4F, and 5F. As noted above, as the surgical fastener 28 is deployed into tissue, the legs 28b return towards the initial closed loop shape due to either super-elasticity or a shape memory property of the surgical fastener, see FIG. 6E. After the surgical fastener has been deployed, the pusher 24 and the spreader 18 are retracted to their initial positions and the next surgical fastener is positioned in the deployment position for subsequent deployment.

Figure 7:
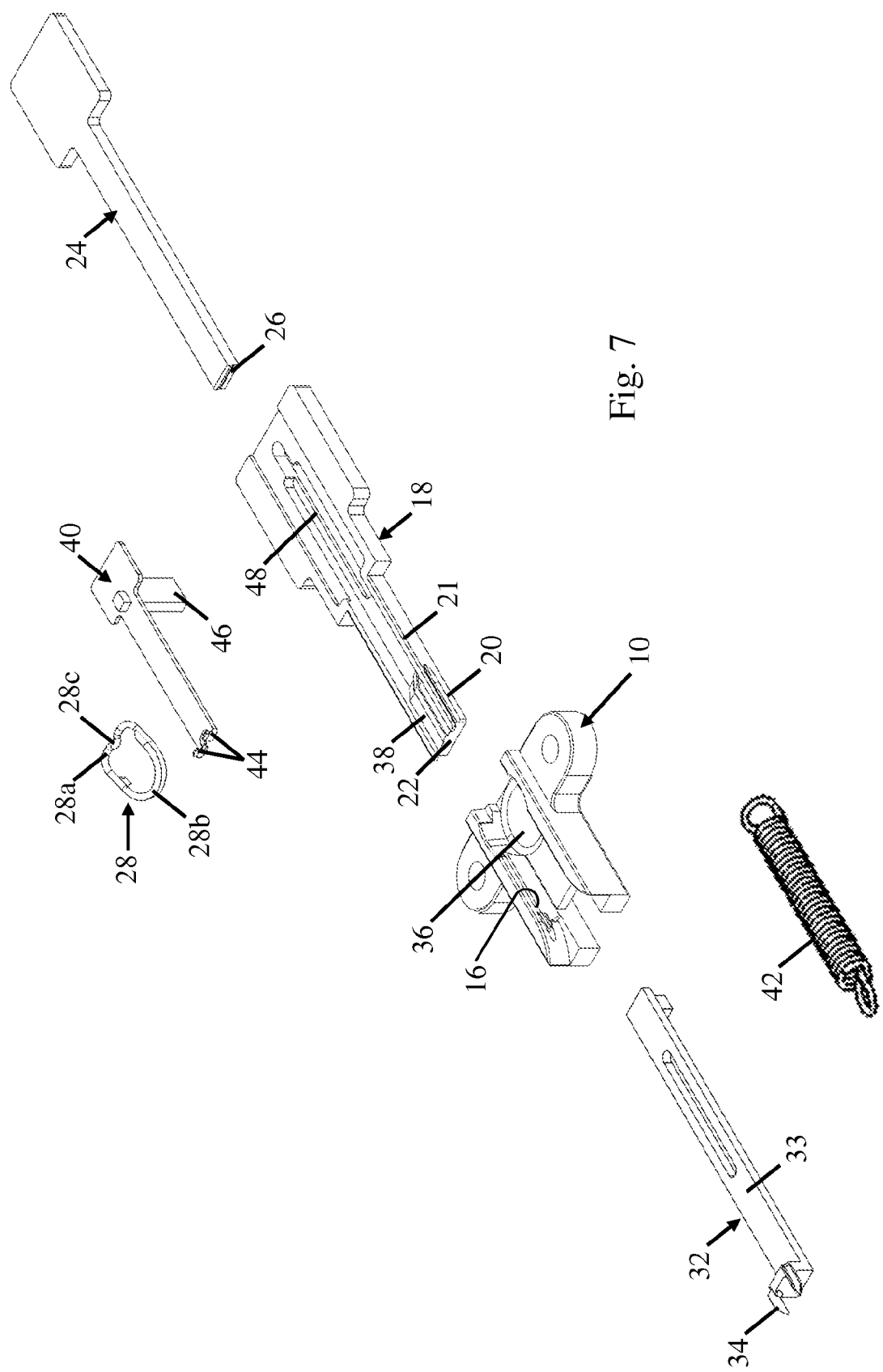
FIG. 7 is an exploded schematic perspective view of a deployment mechanism.
Figure 8:
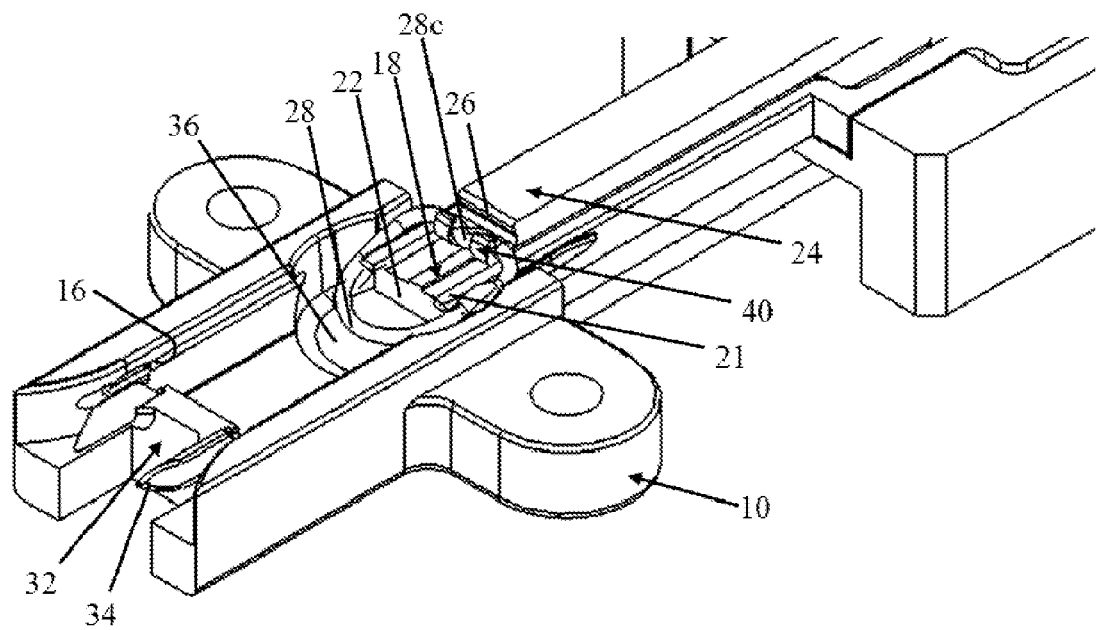
FIG. 8 is a schematic perspective view of a deployment mechanism.
Figure 9A:
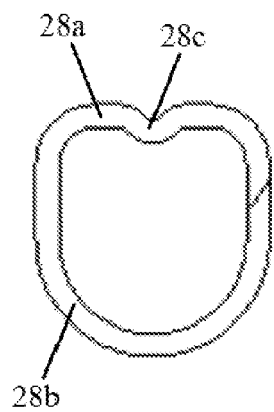
FIG. 9A is a schematic front view of a surgical fastener.
Figure 9B:
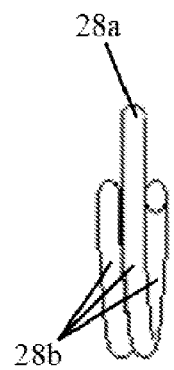
FIG. 9B is a schematic side view of the surgical fastener of FIG. 9A.
Figure 9C:
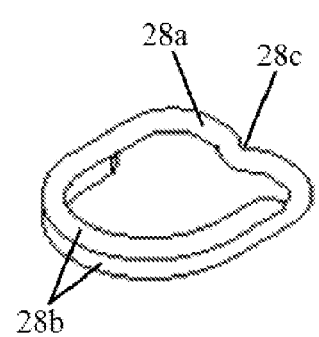
FIG. 9C is a schematic perspective view of the surgical fastener of FIG. 9A.

FIGS. 7-10E are directed to another embodiment of a deployment device. FIGS. 7 and 8 best illustrate the components of this deployment device and their relative arrangements. Similar to the above embodiment, the deployment device includes a former 10, a spreader 18, and a pusher 26. However, in this embodiment, the deployment device includes a separate deflectable hook 40 that acts as a restraining mechanism for selectively preventing distal movement of a surgical fastener 28. The deployment device also includes an extendable cannula 32 that is biased towards a retracted position by an associated return spring 42.

As depicted in the figures, the surgical fastener 28 again includes a back span 28a and a pair of legs 28b extending in a distal direction from opposing ends of the back span. The legs are also curved inwards and overlap each other for at least a portion of their lengths, see FIGS. 7-9C. However, unlike the previous embodiment, the back span 28a is located in, or just slightly above, the same plane in which the legs will be deployed. Therefore, the legs 28b do not include a downwards bend at their connection with the back span 28a. Without wishing to be bound by theory, by arranging the back span 28a in the same plane in which the legs will be deployed, a force can be applied to the surgical fastener without an associated moment being applied to the surgical fastener which may help to avoid rotation and misalignment of the surgical fastener during deployment. The surgical fastener 28 also includes a distally extending dimple 28c located at a midpoint of the back span 28a which helps to position the surgical fastener 28 on the deflectable hook 40 and may help to prevent tilting and/or rotation of the surgical fastener while it is held thereon.

The former 10 may be fixed relative to the elongated shaft. The former 10 includes an anvil 16 that is constructed and arranged to form the surgical fastener into a straight open configuration as compared to spreading the legs further apart as in the previous embodiment. The former 10 also includes a round depression 36 shaped to accommodate a surgical fastener corresponding to an initial deployment position of a distal most surgical fastener.

The spreader 18 includes a distal end 22 constructed and arranged to engage the legs 28b of the surgical fastener to spread them to an open position. However, in this embodiment, the distal end 22 is a flat surface and the grooves 20 for guiding the surgical fastener during opening and deployment do not wrap around the distal end of the spreader and instead only extend proximally from the distal end along the sides of the spreader 18. It should be understood that a spreader with a different shape at the distal end and/or a different arrangement of the grove might be used. For example, a spreader including a rounded distal end and/or a groove that extends around the distal end similar to that described above is contemplated. The spreader 18 also includes two overhangs 21 that extend distally along the upper side edges of the spreader 18 for retaining the surgical fastener 28 during deployment. The overhang 21 again retains the surgical fastener 28 by preventing the upward movement of the legs 28b of the surgical fastener until they have been moved to the open position. The spreader 18 also includes a camming surface 38 adapted to move the restraining mechanism between an open and restraining position. As depicted in the figures, the camming surface 38 extends along a portion of an upper surface of the spreader 18 in a proximal direction from the distal end 22 of the spreader. A slot 48 passes through the upper and lower surfaces of the spreader 18 and is elongated in the axial direction.

The pusher 24 includes a slot 26 located on a distal face of the pusher. The slot 26 is sized and shaped to engage the back span 28a of the surgical fastener and prevents vertical displacement of the back span while they are engaged. Due to the slot 26 being located on the distal face of the pusher, the pusher 24 does not act as a restraining mechanism against distal movement of the surgical fastener back span in this embodiment.

In this embodiment, the restraining mechanism for selectively preventing distal movement of the surgical fastener back span 28a is provided by the deflectable hook 40. As described in more detail below, the use of a deflectable hook to selectively prevent the distal movement of the surgical fastener back span 28a permits the use of a back span 28a located in substantially the same plane in which the legs are deployed. As illustrated in figures, the deflectable hook 40 includes two fingers 44 that are sized and positioned to engage the back span 28a of the surgical fastener on either side of the dimple 28c. It should be understood that while two fingers have been shown, any number fingers could be used. The deflectable hook 40 is biased downwards such that it cams against the camming surface 38 on the spreader 18 in order to selectively control restraint of the surgical fastener during deployment as described in more detail below. The deflectable hook 40 also includes a post 46 which is sized and shaped to pass through the slot 48 of the spreader 18 while permitting distal movement of the spreader during actuation.

An extendable cannula 32 includes two partial cannula 34 located at a distal end of an elongated beam 33. During actuation, the partial cannulas 34 are extended out of the deployment device and into adjacent tissue. The partial cannula 34 are sized and shaped to accommodate the legs 28b of the surgical fastener. Since the legs 28b of the surgical fastener are attached to the back span 28a, the partial cannulas 34 include open sides to permit the legs to pass there through while the back span is able to pass over them. Without wishing to be bound by theory, the extendable cannula 32 may help to avoid buckling of the surgical fastener as it is inserted into a prosthetic and/or tissue since it guides the surgical fastener during the initial insertion into the tissue. The extendable cannula 32 may also result in better tissue bite and depth of purchase as well as a straighter deployment. The use of an extendable cannula may be of particular benefit when the surgical fasteners are deployed in harder tissues and/or through dense prosthetic materials though this embodiment could be used with any appropriate tissue and/or prosthetic. With appropriate modifications to control deployment of the individual cannulas in different angled directions corresponding to the anvil's shape, the concept of extendable cannulas to help guide the surgical fastener as it is deployed into tissue could also be used with the embodiment described above with regards to FIGS. 2-6E.

The relative positioning of the above components for deploying a surgical fastener are illustrated in FIG. 8. An elongated beam 33 of the extendable cannula 32 is movably attached to a bottom surface of the former 10 at the distal end of the deployment device in such a way that it is able to move in a distal direction. When assembled with the former 10, the partial cannula 34 are aligned with the grooves of the anvil 16. As noted above, the return spring 42, not depicted in this figure, is attached to the extendable cannula 32 and the former 10, or other component, to bias the extendable cannula in a proximal direction. The spreader 18 is also disposed on the former 10 and has a distal end 22 positioned in an initial deployment position. The deflectable hook 40 is disposed on the spreader 18 and is fixedly mounted relative to the former 10 such that it is does not move in the distal direction. A bottom surface of the deflectable hook 40 is biased against the camming surface 38 of the spreader 18, with the post 46 positioned in the slot 48 of the spreader. The post 46 and slot 48 are both constructed and arranged to permit distal movement of the spreader 18 while the deflectable hook remains fixed in position. The pusher 24 is disposed on top of the deflectable hook 40 and is also movable in a distal direction relative to the former 10.

In FIGS. 10A-10E which depict the deployment device and the surgical fastener during different stages of deployment. Prior to actuation, a distal most surgical fastener 28 is positioned in an initial deployment position 36 of the former 10, see FIG. 10A. Additionally, the extendable cannula 32, spreader 18, and pusher 24 are positioned in retracted proximal positions. A back span 28a of the surgical fastener is retained by the fingers 44 of the deflectable hook 40. As depicted in these figures, the dimple 28c of the surgical fastener is located between the fingers 44 which may help to prevent rotation and misalignment of the surgical fastener 28 when retained by the deflectable hook 40. The legs 28b of the surgical fastener are engaged by the distal end 22 of the spreader 18. The slot 26 located on the distal face of the pusher 24 is engaged with the back span 28a of the surgical fastener and may help to prevent vertical movement of the back span relative to the pusher during deployment.

With the surgical fastener in the initial deployment position 36, the deployment device is actuated and the spreader 18 is moved in a distal direction, see FIG. 10B. Applying a distally directed force to the legs 28b of the surgical fastener. Simultaneously, the deflectable hook 40 is held in the restraining position by the camming surface 38. Consequently, as the back span 28a is held stationary, the distally directed force deforms the legs 28b towards the open position. The legs 28b are pressed against the grooves of anvil 16 to a straight open position. Additionally, the overhangs 21 and the grooves 20 of the spreader 18 maintain the legs 28b of the surgical fastener in the open position. Distal movement of the spreader 18 continues with the spreader 18 applying a distally directed force to the extendable cannula 32, see FIG. 10C, causing the partial cannulas 34 to extend out of a distal end of the deployment device and into an adjacent tissue and/or prosthetic. As the spreader is moved in the distal direction, the camming surface 38 of the spreader is displaced past the deflectable hook 40 allowing the deflectable hook 40 to move to the open position and release the back span 28a of the surgical fastener, see FIG. 10D. Further distal displacement of the pusher 24 forces the back span 28b of the surgical fastener down the shaft. As the surgical fastener 28 is distally displaced by the pusher 24, the legs 28b pass through the grooves of anvil 16 and into the partial cannulas 34 of the extendable cannula 32. As noted above, the partial cannulas 34 are open on their exterior faces. Therefore, as the legs 28b of the surgical fastener pass through the partial cannulas and into the adjacent tissue and/or prosthetic, the back span 28a of the surgical fastener is able to pass above the partial cannulas 34. Distal displacement of the pusher 24 continues until it has reached its distal most position and the surgical fastener is released from the deployment device, see FIG. 10E. Similar to the prior embodiment, as the surgical fastener 28 is deployed into tissue, the legs 28b return towards the initial closed loop shape due to either superelasticity or a shape memory property of the surgical fastener. It should be noted that in the current embodiment, the back span 28a is displaced along a single plane and is not cammed in a vertical or horizontal direction in order to release the surgical fastener. However, embodiments in which the surgical fastener 28 is cammed to release it from the deployment device are also possible.

After the surgical fastener has been deployed, the spreader 18 and pusher 24 are retracted in the proximal direction. In response to the spreader retracting, the extendable cannula 32 is also retracted in the proximal direction by the associated return spring, not depicted. The deflectable hook 40 is then cammed upwards to the retaining position as the camming surface 38 of the spreader engages the lower surface of the deflectable hook 40. Once each of these components are positioned for the next actuation, the next distal most surgical fastener is positioned for deployment.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A deployment device comprising:
    a handle;
    an elongated shaft extending from the handle, at a distal portion of the shaft:
    a restraint that temporarily limits distal movement of a back span of a surgical fastener, the surgical fastener including two legs extending in a distal direction from opposing ends of the back span, wherein the legs have a first closed position with a first shape;
    a spreader that engages the legs of the surgical fastener in the first closed position, wherein moving the spreader in a distal direction relative to the back span spreads the legs of the surgical fastener from the first closed position to a second open position as the back span is limited from moving distally by the restraint; and
    an anvil, wherein as the surgical fastener is deployed in a distal direction, the legs are formed against the anvil, and wherein the anvil forms the legs to a second shape with a width that is larger than a width of the first shape.

2. The deployment device of claim 1, wherein the restraint temporarily prevents distal movement of the back span.

3. The deployment device of claim 1, wherein the first shape is a closed loop.

4. The deployment device of claim 1, wherein the restraint releases the back span after the spreader spreads the legs of the surgical fastener to the open position.

5. The deployment device of claim 1, wherein the restraint comprises a hook that temporarily prevents movement of the back span.

6. The deployment device of claim 1, further comprising a pusher that pushes the back span of the surgical fastener in a distal direction to deploy the surgical fastener.

7. The deployment device of claim 6, wherein the restraint is the pusher.

8. The deployment device of claim 1, further comprising a ramp that engages the back span to release the surgical fastener during deployment.

9. The deployment device of claim 1, wherein the spreader includes one or more grooves that guide the legs of the fastener as the spreader is moved in the distal direction.

10. The deployment device of claim 1, further comprising the surgical fastener.

11. The deployment device of claim 1, wherein the restraint engages the back span in a first plane, and the spreader engages the legs in a second plane different from the first plane.

12. A deployment device comprising:
a surgical fastener;
a handle;
an elongated shaft extending from the handle, at a distal portion of the shaft:
a restraint that engages a back span of the surgical fastener to temporarily limit distal movement of the back span, the surgical fastener including two legs extending in a distal direction from opposing ends of the back span, wherein the legs have a first closed position with a first shape; and
a spreader configured and arranged to engage the legs of the surgical fastener in the first closed position, wherein moving the spreader in a distal direction relative to the back span spreads the legs of the surgical fastener from the first closed position to a second open position as the back span is limited from moving distally by the restraint, wherein the restraint engages the back span in a first plane and the spreader engages the legs in a second plane different from the first plane.

13. The deployment device of claim 12, wherein the restraint is disposed on the spreader.

14. The deployment device of claim 12, wherein the restraint temporarily prevents distal movement of the back span.

15. The deployment device of claim 12, wherein the first shape is a closed loop.

16. The deployment device of claim 12, wherein the restraint releases the back span after the spreader spreads the legs of the surgical fastener to the open position.

17. The deployment device of claim 16, wherein the spreader includes a camming surface that controls the restraint.

18. The deployment device claim 12, wherein the restraint comprises a deflectable hook that temporarily prevents movement of the back span.

19. The deployment device of claim 12, further comprising a pusher that pushes the back span of the surgical fastener in a distal direction to deploy the system of surgical fastener.

20. The deployment device of claim 19, wherein the restraint is the pusher.

21. The deployment device of claim 12, further comprising a ramp that engages the back span to release the surgical fastener during deployment.

22. The deployment device of claim 12, further comprising an anvil, wherein as the surgical fastener is deployed, the legs are formed against the anvil.

23. The deployment device of claim 22, wherein the anvil forms the legs to a second shape with a width that is larger than a width of the first shape.

24. The deployment device of claim 12, wherein the spreader includes one or more grooves that guide the legs of the fastener as the spreader is moved in the distal direction.

25. The deployment device of claim 12, further comprising cannulas that guide the legs of the surgical fastener as they are deployed.

26. The deployment device of claim 25, wherein the cannulas are selectively extendable from a distal end of the deployment device.

27. The deployment device of claim 25, wherein the cannulas have open sides.

28. The deployment device of claim 27, wherein the open sides of the cannulas permit the legs to pass through the cannulas and the back span to pass over the cannulas.

29. The deployment device of claim 28, wherein the open sides of the cannulas permit the legs to pass through the cannulas and the back span to pass over the cannulas.

30. The deployment device of claim 29, wherein the restraint is disposed on the spreader.

31. A deployment device comprising:
a surgical fastener;
a handle;
an elongated shaft extending from the handle, at a distal portion of the shaft:
a restraint that temporarily limits distal movement of a back span of the surgical fastener, the surgical fastener including two legs extending in a distal direction from opposing ends of the back span, wherein the legs have a first closed position with a first shape;
a spreader that engages the legs of the surgical fastener in the first closed position, wherein moving the spreader in a distal direction relative to the back span spreads the legs of the surgical fastener from the first closed position to a second open position as the back span is limited from moving distally by the restraint; and
an anvil, wherein as the surgical fastener is deployed the legs are formed against the anvil, and wherein the anvil forms the legs to a second shape with a width that is larger than a width of the first shape.

32. The deployment device of claim 31, wherein the restraint temporarily prevents distal movement of the back span.

33. The deployment device of claim 31, wherein the first shape is a closed loop.

34. The deployment device of claim 31, wherein the restraint releases the back span after the spreader spreads the legs of the surgical fastener to the open position.

35. The deployment device of claim 31, further comprising a pusher that pushes the back span of the surgical fastener in a distal direction to deploy the surgical fastener.

36. The deployment device of claim 35, wherein the restraint is the pusher.

* * * * *